United States Patent [19]

Schirmer et al.

[11] Patent Number: 4,761,175
[45] Date of Patent: Aug. 2, 1988

[54] M-ANILIDO-URETHANES AND HERBICIDES CONTAINING THESE COMPOUNDS

[75] Inventors: Ulrich Schirmer, Heidelberg; Rainer Becker, Bad Duerkheim; Bruno Wuerzer, Limburgerhof, all of Fed. Rep. of Germany

[73] Assignee: BASF Aktiengesellschaft, Fed. Rep. of Germany

[21] Appl. No.: 511,016

[22] Filed: Jul. 5, 1983

Related U.S. Application Data

[63] Continuation of Ser. No. 160,432, Jun. 17, 1980, abandoned.

[30] Foreign Application Priority Data

Jun. 28, 1979 [DE] Fed. Rep. of Germany ....... 2926049

[51] Int. Cl.[4] ............................................. A01N 37/44
[52] U.S. Cl. ......................................... 71/100; 71/111; 558/232; 558/234; 558/235; 558/241; 560/27
[58] Field of Search ............. 71/100, 111; 260/455 A; 560/27

[56] References Cited

U.S. PATENT DOCUMENTS 3,979,202  9/1976  Olin et al. ............................. 71/98
4,134,753  1/1979  Horlein ................................. 71/108

OTHER PUBLICATIONS

German Offen. 2,846,625, 5-8-80 (abstract).

Primary Examiner—Catherine L. Mills
Attorney, Agent, or Firm—Keil & Weinkauf

[57] ABSTRACT m-Anilido-urethanes of the formula

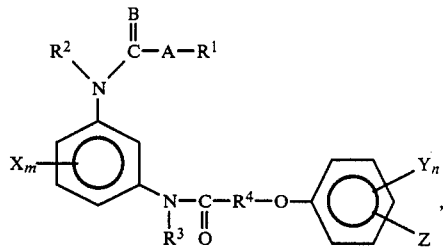

where
A and B independently of one another are oxygen or sulfur,
$R^1$ is alkyl, which is unsubstituted or substituted by halogen, alkoxy, alkoxycarbonyl or cyano, or is alkenyl which is unsubstituted or substituted by halogen, or is alkynyl which is unsubstituted or substituted by halogen or alkoxy, or is cycloalkyl which is unsubstituted or substituted by alkyl, or is aryl,
$R^2$ and $R^3$ are each independently of one another hydrogen, alkyl, alkoxyalkyl or haloalkyl,
$R^4$ is alkylene of 1 to 6 carbon atoms which is unsubstituted or substituted by alkyl, alkoxyalkyl or haloalkyl,
X is hydrogen, alkyl, haloalkyl, alkoxy, halogen, nitro or amino,
Y is hydrogen, alkyl, haloalkyl, alkoxyalkyl, cycloalkyl, aralkyl, halogen, alkoxy, haloalkoxy, alkylthio, nitro, aryl, thiocyanato, cyano,

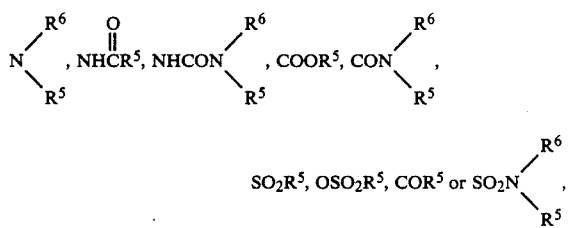

where $R^5$ and $R^6$ are each, independently of one another, hydrogen or have the meanings given for $R^1$, and Z is

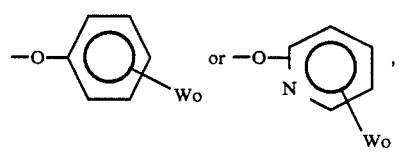

where W has, independently of Y, the meanings given for Y and
m, n and o are numbers from 1 to 4, and herbicides containing these compounds.

3 Claims, No Drawings

M-ANILIDO-URETHANES AND HERBICIDES CONTAINING THESE COMPOUNDS

This is a continuation of application Ser. No. 160,432, filed June 17, 1983, now abandoned.

The present invention relates to novel m-anilido-urethanes, processes for the preparation of these m-anilido-urethanes, herbicides which contain these compounds, and processes for controlling undesired plant growth by means of these compounds.

The use of m-anilido-ureas, eg. 2,4-dichlorophenoxyacetic acid 3'-(N'-dimethyl-ureido)-anilide, as herbicides for controlling undesired broad-leaved and gramineous weeds has been disclosed. However, the literature (German Published Application DAS No. 1,793,226) does not refer to the use of these compounds as selective herbicides. Furthermore, U.S. Pat. No. 3,979,202 discloses a plurality of 3'-(carbamyloxy)-anilides, eg. 3'-N-isopropyl-carbamyloxy-propionanilide, having greatly varying herbicidal actions on higher plants. Further, it is known that phenoxyphenoxycarboxamides (German Laid-Open Application DOS No. 2,632,581) display a herbicidal action, especially against dicotyledonous weeds. In addition, German Laid-Open Application DOS No. 2,531,643 discloses phenoxyphenoxycarboxamides which show a herbicidal action against monocotyledonous plants, without damaging dicotyledonous crops. Germain Laid-Open Applications DOS No. 2,725,146 and DOS No. 2,703,838 disclose m-anilido-urethanes possessing a selective herbicidal action.

We have found that m-anilido-urethanes of the formula

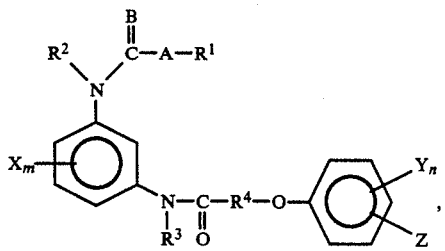

where

A and B independently of one another are oxygen or sulfur, $R^1$ is alkyl, which is unsubstituted or substituted by halogen, alkoxy, alkoxycarbonyl or cyano, or is alkenyl which is unsubstituted or substituted by halogen, or is alkynyl which is unsubstituted or substituted by halogen or alkoxy, or is cycloalkyl which is unsubstituted or substituted by alkyl, or is aryl, $R^2$ and $R^3$ are each independently of one another hydrogen, alkyl, alkoxyalkyl or haloalkyl, $R^4$ is alkylene of 1 to 6 carbon atoms which is unsubstituted or substituted by alkyl, alkoxyalkyl or haloalkyl, X is hydrogen, alkyl, haloalkyl, alkoxy, halogen, nitro or amino, Y is hydrogen, alkyl, haloalkyl, alkoxyalkyl, cycloalkyl, aralkyl, halogen, alkoxy, haloalkoxy, alkylthio, nitro, aryl, thiocyanato, cyano,

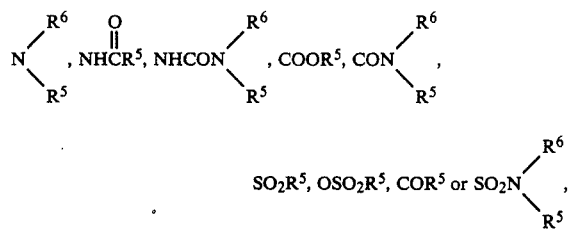

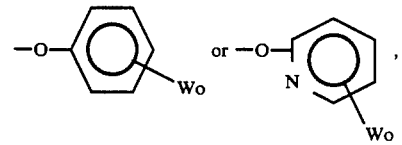

where $R^5$ and $R^6$ are each, independently of one another, hydrogen or have the meanings given for $R^1$, and Z is $$-O-\langle\bigcirc\rangle-W_o \quad \text{or} \quad -O-\langle\bigcirc\rangle-N-W_o,$$

where W has, independently of Y, the meanings given for Y and m, n and o are numbers from 1 to 4, have a good herbicidal action on undesired plants. The action on undesired plants from Gramineae family deserves particular mention. At the same time, important crops are highly insensitive to the novel active compounds.

The radicals shown in the general formula may for example have the following meanings:

$R^1$: alkyl which is unsubstituted or substituted by halogen or alkoxy or alkoxycarbonyl or cyano (eg. methyl, ethyl, 2-chloroethyl, 2-methoxyethyl, methoxycarbonylmethyl, isopropyl, n-propyl, n-butyl, sec.-butyl, tert.-butyl, iso-butyl and cyanomethyl), or alkenyl which is unsubstituted or substituted by halogen (eg. allyl, 1-chloroprop-1-en-3-yl and but-1-en-3-yl), or alkynyl which is unsubstituted or substituted by halogen or alkoxy (eg. propargyl, but-1-yn-3-yl and 1-chlorobut-2-yn-4-yl) or cycloalkyl which is unsubstituted or substituted by alkyl (eg. cyclopentyl, cyclohexyl, 3-methylcyclohexyl, 2,6-dimethylcyclohexyl, cycloheptyl and 4-tert.-butyl-cyclohexyl) or aryl (eg. phenyl), $R^2$ and $R^3$: each, independently of one another, hydrogen, alkyl (eg. methyl, ethyl and iso-propyl), alkoxyalkyl (eg. methoxymethyl and 2-methoxyethyl) and haloalkyl (eg. chloromethyl and 2-chloroethyl), $R^4$: alkylene of 1 to 6 carbon atoms which is unsubstituted or substituted by alkyl, alkoxyalkyl or haloalkyl (eg. methylene, methylmethylene, dimethylmethylene, propylene, hexylene, chloromethylmethylene, methoxymethylmethylene, ethylmethylene, methylethylene, isopropylmethylene, 1-chloromethylethylene, methoxymethylmethylene, 2-chloroethylmethylene, diethylmethylene, ethylene, methylpropylene, butylene, dimethylethylene and propylmethylene), X: hydrogen, alkyl (eg. methyl), haloalkyl (eg. trifluoromethyl), alkoxy (eg. methoxy), halogen (eg. fluorine, chlorine, bromine or iodine), nitro and amino, and Y and W, independently of one another: hydrogen, alkyl (eg. methyl and isopropyl), haloalkyl (eg. trifluoromethyl), alkoxyalkyl (eg. methoxymethyl), cycloalkyl (eg. cyclohexyl), aralkyl (eg. benzyl), halogen (eg. fluorine, chlorine, bromine and iodine), alkoxy (eg. methoxy), haloalkoxy (eg. trifluoromethoxy), alkylthio (eg. methylthio), nitro, aryl (eg. phenyl), thiocyanato, cyano,

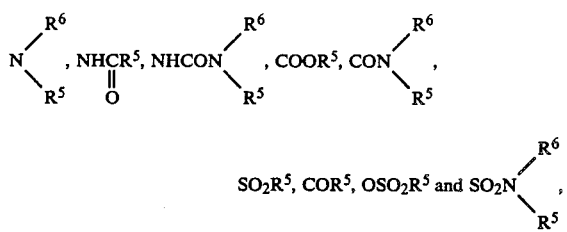

where $R^5$ and $R^6$, independently of one another, are hydrogen or have the meanings given for $R^1$.

The novel compounds may be prepared, for example, by methods shown in the charts which follow, in which A, B, $R^1$, $R^2$, $R^3$, $R^4$, X, Y, Z, m and n have the above meanings. Where urethanes and chloroformic acid esters are referred to in the text which follows, these collective terms also include, respectively, thionourethanes, thiourethanes and dithiourethanes, and chloroformic acid thionoesters, chloroformic acid thioesters and chloroformic acid dithioesters.

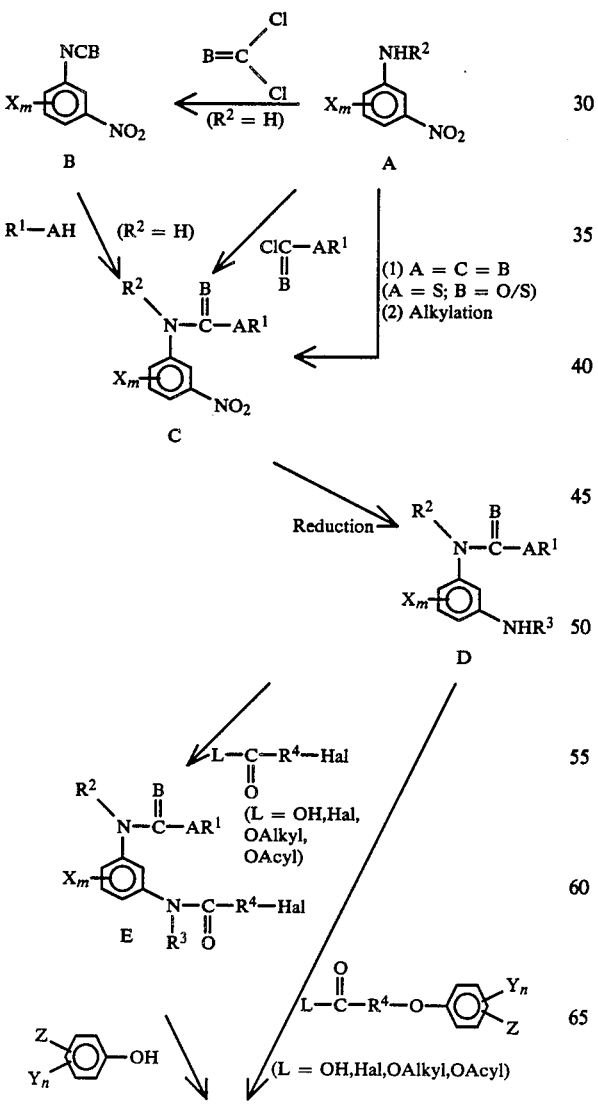

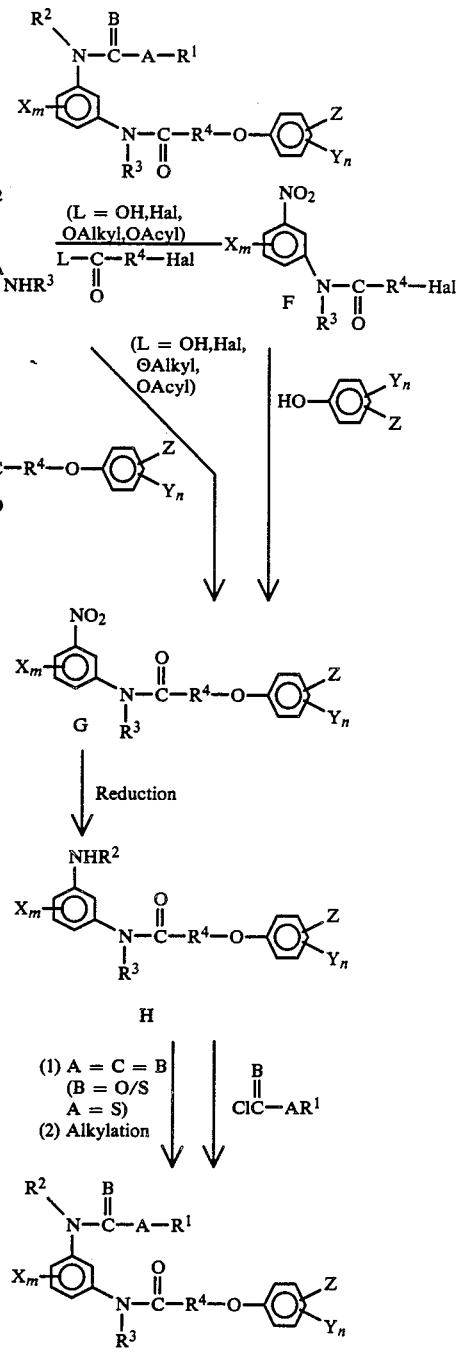

The reaction schemes shown clearly indicate the inter-relations of the starting materials. They also clearly show that one or other method may be more advantageous depending on the nature of the substituents A, B, $R^1$, $R^2$, $R^3$, $R^4$, X, Y and Z and on the availability of the particular reactants.

Starting from the known meta-nitroanilines (A), meta-nitrophenyl iso(thio)cyanates (B) can be prepared (W. Siefken, Ann. Chem. 562 (1949), 75 et seq.), and these, in turn, react smoothly with the components $R^1$—AH to give the nitro(thio)urethanes (C) (S. Petersen in Methoden der Organ. Chemie, Volume VIII, page 131, Georg-Thieme-Verlag, Stuttgart, 4th edition (1952)); the latter are however also directly obtainable from the meta-nitroanilines (A) by reaction with chloroformic acid esters ($R^1A$—CB—Cl) (Germain Laid-Open Application DOS No. 1,643,763) or with carbon disulfide or carbon oxysulfide, a base and an alkylating agent (Methoden der Organ. Chemie, Volume IX, page 831 et seq., Georg-Thieme-Verlag, Stuttgart, 4th edition, 1955). Subsequent reduction gives the aminourethanes (D, $R^3=H$) (S. Schröter in Methoden der Organ. Chemie, Volume XI/1, page 350 et seq., Georg-Thieme-Verlag, Stuttgart, 4th edition 1957) which are acylated, either directly or after conversion to the product monosubstituted at the amino nitrogen (D, $R^3 \neq H$) (Methoden der Organ. Chemie, Volume XI/1, page 24 et seq., Georg-Thieme-Verlag, Stuttgart, 4th edition 1957), by means of phenoxycarboxylic acids, phenoxycarboxylic acid halides, phenoxycarboxylic acid esters or phenoxycarboxylic acid anhydrides to give the novel m-anilido-urethanes (Methoden der Organ. Chemie, Volume XI/2, page 3 et seq., Georg-Thieme-Verlag, Stuttgart, 4th edition, 1958).

The aminourethanes (D) can also first be reacted with a halocarboxylic acid, halocarboxylic acid halide, halocarboxylic acid ester or halocarboxylic acid anhydride, to give the m-anilido-urethanes (E), which then react with phenols to give the novel m-anilido-urethanes (Methoden der Organ. Chemie, Volume VI/3, page 54 et seq., Georg-Thieme-Verlag, Stuttgart, 4th edition, 1965).

A further possible method of synthesis is to react the m-nitroanilines (A) with phenoxycarboxylic acids, phenoxycarboxylic acid halides, phenoxycarboxylic acid esters or phenoxycarboxylic acid anhydrides to give the m-nitroanilides (G), which are also available via the nitro halides (F).

The reduction of the m-nitroanilides (G) gives the m-aminoanilides (H, $R^2=H$), which can, either directly or after conversion to the product which is monosubstituted at the amino nitrogen (H, $R^2 \neq H$) be reacted with chloroformic acid esters ($R^1ACB$—Cl) or with carbon disulfide or carbon oxysulfide, a base and an alkylating agent, to give the novel m-anilido-urethanes.

The preferred synthesis steps are described in more detail below:

(a) The reaction of 3-nitrophenyl iso(thio)cyanates (B) is carried out with or without a conventional catalyst for iso(thio)cyanate reactions, eg. a tertiary amine (triethylamine or 1,4-diazabicyclo-(2,2,2)-octane), a nitrogen-containing heterocyclic compound (pyridine or 1,2-dimethylimidazole) or an organic tin compound (dibutyl-tin diacetate or dimethyl-tin dichloride), in the presence or absence of a solvent which is inert under the reaction conditions, eg. a hydrocarbon (naphtha, gasoline, toluene, pentane or cyclohexane), a halohydrocarbon (methylene chloride, chloroform, dichloroethane, chlorobenzene or o-, m- or p-dichlorobenzene), a nitrohydrocarbon (nitrobenzene or nitromethane), a nitrile (acetonitrile, butyronitrile or benzonitrile), an ether (diethyl ether, tetrahydrofuran or dioxane), an ester (ethyl acetate or methyl propionate), a ketone (acetone or methyl ethyl ketone) or an amide (dimethylformamide or formamide) (Germain Laid-Open Application DOS No. 1,568,138) at from 0° to 150° C., preferably from 40° to 100° C.

(b) 3-Nitroanilines (A) or 3-aminoanilides (H) are reacted with chloroformic acid esters in a suitable solvent, for example water or an alcohol (methanol, ethanol or isopropanol), or as described under (a), in the presence of a conventional acid acceptor, for example an alkali metal hydroxide, carbonate or bicarbonate, alkaline earth metal oxide, hydroxide, carbonate or bicarbonate or tertiary organic base (eg. triethylamine, pyridine, N,N-dimethylamine, N,N-dimethylcyclohexylamine, quinoline or tributylamine) or an excess of the starting material 3-nitroaniline, at from −20° to 150° C., preferably from 20° to 80° C.

(c) The reduction of the nitrourethanes (C) or nitroanilides can be carried out in accordance with one of the conventional processes, for example by catalytic hydrogenation, by using a combination of a metal and an acid, for example of iron and an acid, or by using a combination of a metal and an alcohol, for example zinc dust and aqueous alcohol or iron and aqueous alcohol.

(d) 3-Nitroanilines (A) or aminourethanes (D) are reacted with phenoxycarboxylic acid halides or with halocarboxylic acid halides in a suitable solvent, in the presence of a conventional acid acceptor, as described under (a), at from −20° to 150° C., preferably at 0°–60° C.

Instead of the acid halides, the acids themselves can also be employed, provided these are activated with an aliphatic carbodiimide, eg. dicyclohexylcarbodiimide. Amongst the solvents mentioned under (a), ethers, eg. tetrahydrofuran, are particularly suitable, and in these the reaction is preferably carried out at from 0° to 60° C.

The reaction of the 3-nitroanilines (A) or aminourethanes (D) with phenoxycarboxylic acid esters is carried out either in the absence of a solvent or in an inert solvent such as a hydrocarbon (toluene), a halohydrocarbon (dichlorobenzene) or an amide (dimethylformamide) at from 50° to 180° C., preferably from 80° to 150° C.

(e) The haloamidourethanes (E) or nitrohaloamides (F) are reacted either with alkali metal phenolates in an inert solvent, as described under (a), or with finely powdered potassium carbonate and phenol in a ketone (acetone or methyl ethyl ketone) at from 0° to 150° C., preferably from 40° to 100° C.

The Examples which follow illustrate the preparation of the novel m-anilido-urethanes and of their precursors:

I. Nitrourethanes

Example A 87 parts by weight of sodium bicarbonate are added to 138 parts by weight of m-nitroaniline in 500 parts by weight of tetrahydrofuran (THF). 120 parts by weight of thiomethyl chloroformate are added dropwise at room temperature, whilst stirring; the mixture is then stirred for a further 16 hours at room temperature and is filtered, the solvent is distilled off in a rotary evaporator and the oil obtained is stirred into toluene. The crystals which separate out are filtered off and dried. Melting point: 137°–138° C.

The compound has the following structural formula:

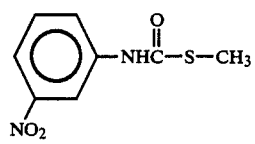

Example B 51 parts by weight of tert.-butanol are added to 112 parts by weight of 3-nitrophenyl isocyanate in 600 parts by weight of toluene. After 4 hours, a few drops of triethylamine are added and the mixture is left to stand for 48 hours. After stripping off the solvent under reduced pressure, white crystals are obtained.

Melting point: 97°-99° C.

The compound has the following structural formula:

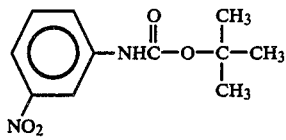

The following nitrourethanes (C) can be prepared by corresponding processes:

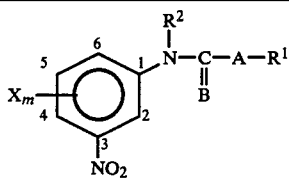

| A | B | X | R¹ | R² | Melting point, °C. |
|---|---|---|---|---|---|
| O | O | H | CH₃ | H | 153-155 |
| O | S | H | CH₃ | H | |
| O | O | 6-CH₃ | CH₃ | H | 132-133 |
| O | O | H | Phenyl | H | 123-125 |
| O | O | H₃ | Phenyl | CH₃ | 69-70 |
| O | O | 6-F | Phenyl | H | 138-140 |
| O | O | 5-CF₃ | CH₃ | H | 86-87 |
| O | O | 6-CH₃ | C₂H₅ | H | 131-133 |
| O | O | H | C₂H₅ | H | 64-66 |
| O | O | 2-CH₃ | Phenyl | H | 112-114 |
| O | O | 4-CH₃ | CH₃ | H | 114-117 |
| O | O | H | Cyclooctyl | H | 103-105 |
| O | O | H | CH₂COOCH₃ | H | 123-125 |
| O | O | 5-CF₃ | CH(CH₃)₂ | H | 121-123 |
| O | O | H | CH₃ | CH₃ | 58-61 |
| O | O | H | 3,5-Dimethylcyclohexyl | H | 128-129 |
| O | O | H | CH(CH₃)₂ | H | 86-88 |
| O | O | 6F | CH₃ | H | 116-118 |
| O | O | 4Cl | Phenyl | H | 125-127 |
| O | O | 4Cl | CH₃ | H | 122-124 |
| O | O | 4-CH₃ | C₂H₅ | H | 80-81 |
| O | O | H | 1-Methylcyclopentyl | H | 57-59 |
| O | O | 5-CF₃ | Phenyl | H | 133-135 |
| O | O | H | 2,6-Dimethylcyclohexyl | H | 121-123 |
| O | O | 6OCH₃ | CH₃ | H | 134-136 |
| O | O | H | Cycloheptyl | H | 102-104 |
| O | O | 6OCH₃ | Phenyl | H | 209-211 |
| O | S | H | Phenyl | H | |
| O | O | H | Cyclopentyl | H | 110-112 |
| O | O | 6Cl | CH₃ | H | 136-138 |
| O | O | H | 3-Methylcyclohexyl | H | 120-122 |
| S | S | H | CH₃ | H | |
| S | O | H | C(CH₃)₃ | H | |
| S | O | H | C₂H₅ | H | |
| S | O | H | Phenyl | H | 156-158 |
| O | O | C₂H₅ | Phenyl | H | 56-58 |
| O | O | H | C(CH₃)₂C₂H₅ | H | 62-63 |
| O | O | H | CH(CH₂OCH₃)₂ | H | 95-96 |
| O | O | H | Cyclohexyl | H | 117-118 |

II. Aminourethanes

Example C 40 parts by weight of 3-(S-methylthiocarbamyl)nitrobenzene are added, with vigorous stirring, to a mixture, heated to 80° C., of 33 parts by weight of iron powder, 75 parts by weight of alcohol, 60 parts by weight of water and 3 parts by weight of concentrated hydrochloric acid, the addition being made in such portions that the temperature of 80° C. is maintained without external heating. The mixture is then refluxed for 1 hour and filtered hot, the residue is digested and the filtrate is extracted with about 1,000 parts by weight of methylene chloride, the methylene chloride phase is dried over sodium sulfate and concentrated, and the residue is recrystallized from toluene.

Melting point: 101°-103° C.

Structure:

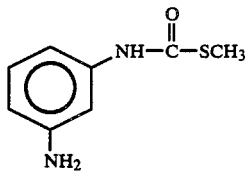

The following aminourethanes (D) can be prepared by corresponding processes:

| A | B | X | R¹ | R² | Melting point, °C. |
|---|---|---|---|---|---|
| O | O | H | CH₃ | H | 87-89 |
| O | O | 6CH₃ | CH₃ | H | |
| O | O | 4F | Phenyl | CH₃ | 70-72 |
| O | O | 4F | CH₃ | H | |
| O | S | H | CH₃ | H | |
| S | O | H | C₂H₅ | H | |
| O | S | H | Phenyl | H | |
| O | O | 5CF₃ | CH₃ | H | viscous oil |
| O | O | H | C₂H₅ | H | viscous oil |
| O | O | 2CH₃ | Phenyl | H | 131-133 |
| O | O | 4CH₃ | CH₃ | H | |
| O | O | 4Cl | Phenyl | H | 215-217 |
| O | O | 4Cl | CH₃ | H | |
| O | O | 4CH₃ | C₂H₅ | H | |
| S | S | H | Phenyl | H | |
| O | O | H | 3,3,5-Trimethylcyclohexyl | H | 100-102 |
| O | O | H | Phenyl | C₂H₅ | 104-106 |
| O | O | H | Cyclopentyl | H | |
| O | O | 5-CF₃ | Phenyl | H | 214-216 |
| O | O | H | Phenyl | H | 178-180 |
| O | O | H | 1-Methylcyclopentyl | H | |
| O | O | H | Hexahydrobenzyl | H | 106-108 |
| O | O | 6OCH₃ | CH₃ | H | 85-87 |
| O | O | H | Cycloheptyl | H | 86-88 |
| O | O | 6OCH₃ | Phenyl | H | 84-86 |
| O | O | 6Cl | CH₃ | H | |
| O | O | H | 3-Methylcyclohexyl | H | 95-97 |
| O | O | H | CH₂COOCH₃ | H | viscous oil |
| S | S | H | CH₃ | H | |
| O | O | H | C(CH₃)₃ | H | 109-110 |
| O | O | 5-CF₃ | CH(CH₃)₂ | H | 102-104 |
| O | O | H | CH₃ | CH₃ | 89-92 |
| O | O | H | 3,5-Dimethylcyclohexyl | H | 80-82 |
| O | O | H | CH(CH₃)₂ | H | 66-68 |
| O | O | 4F | CH₃ | H | |
| O | O | H | C(CH₃)₂C₂H₅ | H | 65-67 |
| O | O | H | Cyclohexyl | H | 122-124 |

III. Nitrohaloamides and haloamidourethanes

Example D 126 parts by weight of sodium bicarbonate are added to 138 parts by weight of 3-nitroaniline in 1,500 parts by weight of ethyl acetate. 216 parts by weight of 2-bromopropionyl bromide are added dropwise at 0°–10° C., with stirring, the mixture is then stirred for a further 16 hours at room temperature and is filtered, the filtrate is concentrated and the crystals obtained are washed with toluene. Melting point: 99°–101° C.

The compound has the following structural formula (cf. F)

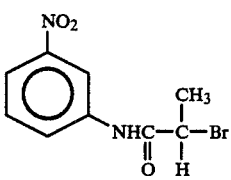

The following haloamidourethanes (E) can be prepared by corresponding processes:

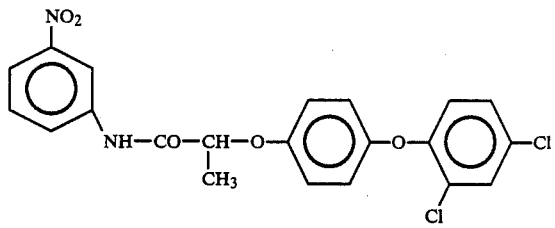

Example F

A mixture of 295 parts by weight of α-(2,4-dichlorophenoxyphenoxy)-propionyl-m-nitroanilide, 5 parts by weight of a 10% strength palladium/charcoal mixture and 1,500 parts by weight of tetrahydrofuran is hydrogenated at room temperature (20° C.) under 100 bar hydrogen pressure. After the absorption of hydrogen has ceased, the mixture is filtered, the filtrate is concentrated, the residue is taken up in anhydrous ethanol and the solution is saturated with HCl gas. The hydrochloride is then precipitated with ether, and is filtered off. Melting point of the hydrochloride: 125°–128° C. (with decomposition).

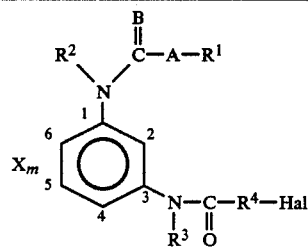

| A | B | X | $R^2$ | $R^1$ | $R^3$ | $R^4$ | Hal | Melting point °C. |
|---|---|---|---|---|---|---|---|---|
| O | O | H | H | Methyl | H | —CH(CH₃)— | Cl | 138–141 |
| O | O | H | H | Methyl | H | —CH₂— | Cl | 168–170 |
| S | S | H | H | Methyl | H | —C(CH₃)— | Cl | |
| O | O | H | H | Methyl | H | —C(CH₃)₂—CH₂— | Cl | 125–127 |
| O | O | H | H | Methyl | H | —CH(C₂H₅)— | Br | 131–133 |
| O | O | H | H | Ethyl | H | —CH₂— | Cl | |
| O | O | H | H | Methyl | H | —C(CH₃)₂— | Br | 91–93 |
| O | O | 4CH₃ | H | Methyl | H | —CH(CH₃)— | Br | 207–210 |
| O | O | H | H | Methyl | H | —(CH₂)₃— | Cl | |
| S | O | H | H | Methyl | H | —CH(CH₃)— | Br | 160–162 |
| O | O | H | H | Methyl | H | —CH(CH₃)— | Br | 142–143 |
| O | S | H | H | Methyl | H | —CH(CH₃)— | Br | |
| O | O | H | H | Phenyl | H | —CH₂— | Cl | 170–173 |
| O | O | H | CH₃ | Methyl | H | —CH(CH₃)— | Cl | |
| O | O | H | H | Phenyl | H | —C(CH₃)₂—CH₂— | Cl | 143–145 |
| O | O | H | H | Phenyl | H | —CH(CH₃)— | Cl | 170–172 |
| O | O | H | H | Methyl | CH₃ | —CH(CH₃)— | Br | |

IV. 3-Nitroanilides and 3-aminoanilides

Example E

A mixture of 220 parts by weight of α-bromopropionyl-m-nitroanilide, 206 parts by weight of p-(2,4-dichlorophenoxy)-phenol, 1,000 g of methyl ethyl ketone, 200 g of potassium carbonate and 20 g of potassium iodide is kept under reflux for 10 hours, whilst stirring. It is then cooled and filtered, and the filtrate is concentrated. The solid obtained is recrystallized from ethanol. Melting point: 127°–128° C.

The compound has the following structural formula:

The compound has the following structural formula:

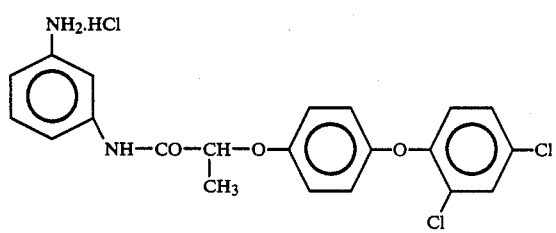

V. m-Anilido-urethanes

EXAMPLE 1

13.6 parts by weight of α-(2,4-dichlorophenoxy-phenoxy)-propionyl-m-aminoanilide hydrochloride and 6.7 parts by weight of sodium bicarbonate are stirred for 30 minutes in 200 parts by weight of tetrahydrofuran, and 4.1 parts by weight of n-butyl chlorocarbonate in 30 parts by weight of tetrahydrofuran are then added dropwise. After 2 hours, the mixture is filtered, the filtrate is concentrated and the residue is chromatographed on silica gel (developer: methylene chloride containing 10% of methanol). A very viscous oil is obtained, which according to the NMR analysis data which follow, has the structure shown below:

| NMR [CDCl₃] | |
|---|---|
| \>CH—CH₃ | $\delta$ = 1.60 (d) |
| \>C$\underline{H}$—CH₃ | $\delta$ = 4.72 (q) |
| O—CH₂—CH₂—CH₂—CH₃ | $\delta$ = 4.16 (t) |
| O—CH₂—CH₂—CH₂—CH₃ | $\delta$ = 1.61 (m) |
| O—CH₂—CH₂—CH₂—CH₃ | $\delta$ = 1.4 (m) |
| O—CH₂—CH₂—CH₂—CH₃ | $\delta$ = 0.95 (t) |

Analysis for $C_{26}H_{26}Cl_2N_2O_5$ (Molecular weight=517): calculated: C: 60.36, H: 5.07, N: 5.41, Cl: 13.70; found: C: 60.6, H: 5.2, N: 5.2, Cl: 13.3.

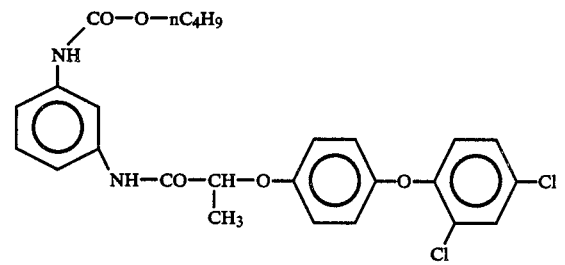

EXAMPLE 2

19.0 parts by weight of α-(2,4-dichlorophenoxy-phenoxy)-propionyl chloride in 125 parts by weight of toluene are added dropwise, at room temperature, to a mixture of 10.4 parts by weight of 3-(O-tert.-butylcarbamyl)-aniline, 5.1 parts by weight of triethylamine and 100 parts by weight of toluene. After 3 hours, the mixture was stirred into ice water and the batch is extracted with ethyl acetate. The ethyl acetate phase is washed with sodium carbonate solution and concentrated. An amorphous solid is obtained; its structure is characterized by the following NMR data in CDCl₃, and elementary analysis:

| —C[CH₃]₃ | $\delta$ = 1.49 (s) |
|---|---|
| \>CH—CH₃ | $\delta$ = 1.58 (d) |
| \>CH—CH₃ | $\delta$ = 4.58 (qu) |

Analysis for $C_{26}H_{26}N_2O_5Cl_2$ (molecular weight=517): calculated: C: 60.36 H: 5.07 Cl: 13.70 N: 5.41; found: C: 60.8 H: 5.4 Cl: 13.3 N: 5.1.

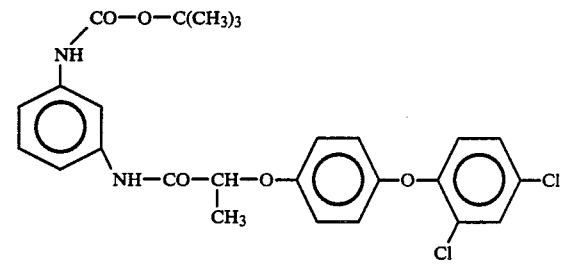

EXAMPLE 3

16.3 parts by weight of α-(2,4-dichlorophenoxy-phenoxy)-propionic acid are dissolved in 200 parts by weight of tetrahydrofuran and 13 parts by weight of dicyclohexylcarbodiimide are added. The mixture is stirred for 2 hours at room temperature and 8.4 parts by weight of 3-(O-methylcarbamyl)-aniline in 80 parts by weight of tetrahydrofuran are then added dropwise. After stirring for 15 hours, the mixture is filtered, the filtrate is concentrated and the oily residue which remains is purified by column chromatography (developer: methylene chloride+5% of methanol).

A solid, of melting point 135° C., having the following structure is obtained:

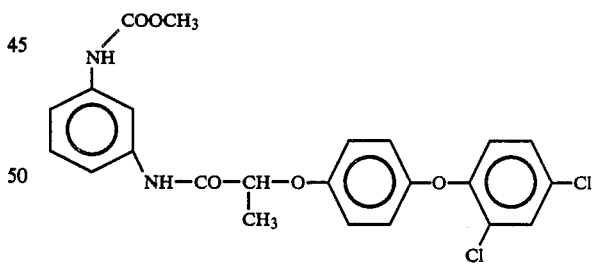

EXAMPLE 4

16.4 parts by weight of α-bromopropionyl-3-(O-methylcarbamyl)-anilide are boiled for 8 hours with 30 parts by weight of potassium carbonate, 1 part by weight of potassium iodide and 14.5 parts by weight of 4-(2'-chloro-4'-nitrophenoxy)-phenol in 200 parts by weight of methyl ethyl ketone. The mixture is filtered, the filtrate is concentrated, the residue is taken up in methylene chloride and this solution is extracted by shaking with dilute sodium hydroxide solution. After drying over sodium sulfate, the solvent is distilled off and the residue is recrystallized from a toluene/cyclohexane mixture.

White crystals of melting point 145°–147° C. are obtained. The compound has the following structural formula:
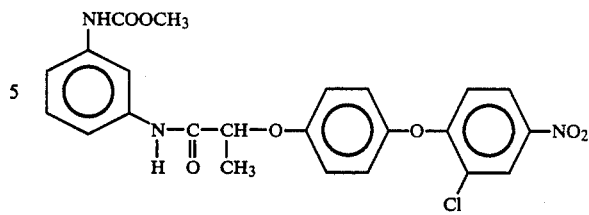
The following compounds can be prepared in a corresponding manner:

| Nr. | A | B | R¹ | R² | R³ | R⁴ | X | Y | Z | m.p.°C. |
|---|---|---|---|---|---|---|---|---|---|---|
| 5 | O | O | CH₃ | H | H | —CH(CH₃)— | H | H | 4-phenoxy | 99 |
| 6 | O | O | C₂H₅ | H | H | —CH(CH₃)— | H | H | 4-(2',4'-dichlorophenoxy) | highly viscous |
| 7 | S | S | CH₃ | H | H | —CH(CH₃)— | H | H | 4-(2',4'-dichlorophenoxy) | 125 |
| 8 | O | O | CH₃ | H | H | —CH₂— | H | H | 4-(4'[trifluoromethyl]phenoxy) | 166 |
| 9 | O | O | i-C₃H₇ | H | H | —CH(CH₃)— | H | H | 4-(2',4'-dichlorophenoxy) | highly viscous |
| 10 | S | O | CH₃ | H | H | —CH₂— | H | H | 4-(2'-nitro-4'-chlorophenoxy) | |
| 11 | O | O | CH₂CH₂Cl | H | H | —(CH₂)₃— | H | 3-Cl | 4-(3'-thiocyanatophenoxy) | 173 |
| 12 | O | O | cycloC₇H₁₃ | H | H | —CH(CH₃)— | H | H | 4-(2',4'-dichlorophenoxy) | highly viscous |
| 13 | O | S | CH₂C≡CH | H | H | —CH(CH₃)— | 4F | H | 4-(2'-methyl-4'-chlorophenoxy) | 169 |
| 14 | O | O | C₂H₅ | H | H | —CH(CH₃)— | H | H | 4-(2',4'-dichlorophenoxy) | 179 |
| 15 | O | O | CH₂CH=CH₂ | H | H | —CH(CH₃)— | H | H | 4-(3'[methoxycarbonyl]phenoxy) | |
| 16 | S | O | i-C₃H₇ | H | H | —C(C₂H₅)₂— | H | H | 4-(2',4'-dichlorophenoxy) | |
| 17 | O | O | CH₂CH₂CN | H | H | —CH(CH₃)— | 6Cl | H | 4-(2'-brom-4'-chlorophenoxy) | highly viscous |
| 18 | O | O | CH₃ | H | H | —CH(nC₃H₇)— | H | H | 4-(2'-nitro-4'-iodophenoxy) | |
| 19 | O | O | C₂H₅ | H | H | —CH(iC₃H₇)— | H | 2Br | 4-(2',4'-diiodophenoxy) | 134-136 |
| 20 | S | O | CH₃ | CH₃ | CH₂OCH₃ | —CH(C₂H₅)— | 5-CH₃ | H | 4-(4'-cyclohexyl)phenoxy) | 126 |
| 21 | O | O | CH₂CN | CH₂OCH₃ | H | —CH₂— | H | H | 4(4'[thiomethyl]phenoxy) | |
| 22 | O | O | CH₃ | H | H | —CH(C₂H₅)— | H | H | 4(4[dimethylamino]phenoxy) | 119 |
| 23 | S | S | C₂H₅ | H | H | —CH(CH₂OCH₃)— | H | H | 3(3'-methylsulfonyl)phenoxy) | 130 |
| 24 | O | O | CH₃ | H | H | —C(CH₃)₂— | H | H | 4(3'[methoxymethyl]phenoxy) | 108 |
| 25 | O | O | i-C₃H₇ | H | H | —CH(CH₃)— | H | H | 4-(2',4'-dichlorophenoxy) | |
| 26 | O | O | C₆H₅ | C₂H₅ | i-C₃H₇ | —CH(CH₃)— | H | H | 4(3'[tetrafluoroethoxy]phenoxy) | |
| 27 | O | S | t-C₄H₉ | H | C₂H₅ | —CH(CH₃)Cl)— | H | 2-CH₃ | 4(2'-thiocyanatophenoxy) | |
| 28 | O | O | C₂H₅ | H | H | —CH₂— | H | H | 4(2'[trifluoromethyl]phenoxy) | |
| 29 | S | O | CH₃ | H | H | —CH(CH₃)— | H | 2-NO₂ | 4(2'-nitro-4'[trifluoromethyl]phenoxy) | |
| 30 | O | O | i-C₃H₇ | H | H | —CH(CH₃)CH₂— | H | 2-Br | 4(2'-chlor-4'[trifluoromethyl]phenoxy) | |
| 31 | O | O | CH₃ | H | H | —CH(CH₃)(CH₂)₂— | 2-CH₃ | H | 4(3'[methoxy]phenoxy) | |
| 32 | O | O | CH₃ | CH₂Cl | H | —(CH₂)₄— | H | 2-CF₃ | 3(3'[dimethylamino]phenoxy) | |
| 33 | O | O | CH₃ | H | H | —CH(CH₃)CH₂— | H | 3-Br | 4(4'[acetyl]phenoxy) | |
| 34 | O | O | CH₃ | H | H | —CH(CH₃)(CH₂)₂— | H | 3-CH₃ | 4(4'[methylaminosulfonyl]phenoxy) | |
| 35 | O | O | CH(CH₃)CH=CH₂ | H | H | —CH(CH₃)— | 4-CH₃ | H | 4(2'-formyl-4'-chlorophenoxy) | |
| 36 | O | O | CH₂C≡CCH₂Cl | H | H | —CH(CH₃)— | H | H | 4(2'-chlor-4'[methylsulfonyl]phenoxy) | |
| 37 | O | O | n-C₃H₇ | H | H | —CH₂— | 4-CH₃ | 2-Cl | 4(2',4'-dichlorophenoxy) | |
| 38 | O | O | CH₃ | H | H | —CH₂— | H | 3-NO₂ | 4(3'-bromophenoxy) | |
| 39 | O | O | CH(CH₃)C≡CH | H | H | —CH(CH₃)— | 6-OCH₃ | H | 4(4'-fluorophenoxy) | |
| 40 | O | O | t-C₄H₉ | H | H | —CH(CH₃)— | H | H | 4(4'-bromophenoxy) | |
| 41 | O | O | CH₃ | H | H | —CH(CH₃)— | 4-OCH₃ | H | 4(2',4'-dichlorophenoxy) | |

-continued

| Nr. | A | B | R¹ | R² | R³ | R⁴ | X | Y | Z | m.p.°C |
|-----|---|---|-----|-----|-----|-----|---|---|---|--------|
| 44 | O | O | CH(CH₂F)₂ | H | H | —CH(CH₃)— | H | H | 4(4'-nitrophenoxy) | 183 |
| 45 | O | O | CH₂CCl=CH₂ | H | H | —CH(CH₃)— | H | H | 3(3'-nitrophenoxy) | |
| 46 | O | O | C₆H₅ | H | H | —CH(CH₃)— | 5-CF₃ | H | 4(2',4'-dichlorophenoxy) | |
| 47 | O | O | CH₂CH₂OCH₃ | H | H | —CH(C₂H₅)— | H | H | 4(4'-chlorophenoxy) | |
| 48 | O | O | cycl.C₅H₉ | H | H | —CH(CH₂OCH₃)— | H | H | 3(3'-chlorophenoxy) | |
| 49 | O | O | CH₂CH₂F | H | H | —(CH₂)₆— | 4-Cl | H | 3(4'-chlorophenoxy) | |
| 50 | O | O | ⬠–CH₂ (cyclopentylmethyl) | H | H | —C(CH₃)₂ | H | H | 3(2,4'-dichlorophenoxy) | |
| 51 | O | O | CH₃ | H | H | —CH(CH₃)— | H | H | 4(4'-fluorophenoxy) | 121 |
| 52 | O | O | sec.C₄H₉ | H | H | —CH(CH₃)(CH₂)₄— | 6-CH₃ | H | 3(2'-nitro-4'-chlorophenoxy) | |
| 53 | O | O | CH₃ | H | H | —CH(CH₃)— | H | H | 4(2'-chloro-4'-bromophenoxy) | 135 |
| 54 | O | O | t-C₅H₁₁ | H | H | —CH(CH₃)— | H | H | 3(2',4'-dibromophenoxy) | |
| 55 | O | O | H₃C–⬠ (1-methylcyclopentyl) | H | H | —CH(CH₃)— | H | H | 3(3'[trifluoromethyl]phenoxy) | |
| 56 | O | O | CH₃ | H | H | —CH(CH₃)— | H | H | 4(4'-chlorophenoxy) | 96-97 |
| 57 | O | O | CH₃ | H | H | —CH(CH₃)— | H | H | 4(2'-nitro-4'-chlorophenoxy) | 152-154 |
| 58 | O | O | CH₃ | H | H | —CH(CH₃)— | H | H | 4(4'-nitrophenoxy) | 73-75 |
| 59 | O | O | CH₃ | H | H | —CH(CH₃)— | H | H | 3(2'-chloro4'-nitrophenoxy) | 142 |
| 60 | O | O | CH₃ | H | H | —CH(CH₃)— | H | H | 4(2'-chloro4'[trifluoromethyl]phenoxy) | 103 |
| 61 | O | O | i-C₃H₇ | H | H | —CH(CH₃)— | H | H | 4(4'[trifluoromethyl]phenoxy) | |
| 62 | O | O | C₂H₅ | H | H | —CH(CH₃)— | H | H | 4(4'[trifluoromethyl]phenoxy) | |
| 63 | S | O | CH₃ | H | H | —CH(CH₃)— | H | H | 4(4'[trifluoromethyl]phenoxy) | |
| 64 | O | O | CH₃ | H | H | —CH(CH₃)— | H | H | 4(4'[trifluoromethyl]phenoxy) | |
| 65 | S | S | CH₃ | H | H | —CH(CH₃)— | H | H | 4(2'-bromo-4'-[trifluoromethyl]phenoxy) | 53 |
| 66 | O | O | CH₃ | H | H | —CH(CH₃)— | H | H | 4(2'[5'-chloropyridyloxy]) | |
| 67 | O | O | CH₃ | H | H | —CH(CH₃)— | H | H | 4(2'[5'-iodopyridyloxy]) | |
| 68 | S | O | CH₃ | H | H | —CH(CH₃)— | H | H | 4(2'[3',5',6'-trichloropyridyloxy]) | |
| 69 | O | S | CH₃ | H | H | —CH(CH₃)— | H | H | 4(2'[5'-bromopyridyloxy]) | |
| 70 | O | O | CH₃ | H | H | —CH(CH₃)— | H | H | 4(2'[3',5'-dichloropyridyloxy]) | |

-continued $$R^2 \underset{X_m}{\overset{B}{\underset{\|}{N}}} \underset{}{\overset{}{\underset{}{\overset{}{\bigcirc}}}} \underset{R^3}{\overset{}{N-C-R^4-O}} \underset{Y_n}{\overset{Z}{\underset{}{\overset{}{\bigcirc}}}}$$

| Nr. | A | B | R¹ | R² | R³ | R⁴ | X | Y | Z | m.p.°C. |
|---|---|---|---|---|---|---|---|---|---|---|
| 71 | O | O | CH₃ | H | H | —CH(CH₃)— | H | H | 4(4'[3'-chloropyridyloxy]) | 144–146 |
| 72 | S | O | CH₃ | H | H | —CH(CH₃)— | H | H | 4(2'[5'-chloropyridyloxy]) | 137–140 |
| 73 | O | O | C₂H₅ | H | H | —CH(CH₃)— | H | H | 4(2'[5'-chloropyridyloxy]) | 88–90 |
| 74 | O | O | t-C₄H₉ | H | H | —CH(CH₃)— | H | H | 4(2'[5'-chloropyridyloxy]) | highly viscous |
| 75 | S | O | CH₃ | H | H | —CH(CH₃)— | H | H | 4(2'-nitro-4'[trifluoromethyl]phenoxy) | 142–146 |
| 76 | O | O | i-C₃H₇ | H | H | CH₂ | H | H | 4(2'-nitro-4'-chlorophenoxy) | 111–113 |
| 77 | O | O | i-C₃H₇ | H | H | —CH(CH₃)— | H | H | 4(2'-chloro-4'-trifluoromethyl-phenoxy) | |
| 78 | S | O | CH₃ | H | H | —CH(CH₃)— | H | H | 4(4'-chlorophenoxy) | |
| 79 | S | O | CH₃ | H | H | —CH(CH₃)— | H | H | 4(2'-chloro-4'-bromophenoxy) | |
| 80 | S | O | CH₃ | H | H | —CH(CH₃)— | H | H | 4(2',4'-dichlorophenoxy) | |

The novel active ingredients can be converted into the conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvent and/or carriers, with or without the addition of emulsifiers and dispersants and, where water is used as the diluent, with or without organic auxiliary solvents. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines e.g., ethanolamine, dimethylformamide, and water; solid carriers, for example natural rock powders, e.g., kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The agents in general contain from 0.1 to 95% by weight of active ingredient, preferably from 0.5 to 90%.

The agents, and the ready-to-use preparations obtained therefrom, e.g., solutions, emulsions, suspensions, powders, dusts, pastes or granules, are applied in conventional manner, e.g. by spraying, atomizing, dusting, broadcasting or watering.

The application rates depend on the composition and growth stages of the weed flora, and vary from 0.1 to 15, and preferably from 0.2. to 3.0, kg of active ingredient per hectare.

The new arylthiolcarbamates may be mixed with each other, or with numerous representatives of other herbicidal or growth-regulating active ingredient groups, and applied in such combinations. These combinations extend the spectrum of action, and synergistic effects are sometimes achieved. Examples of compounds which may be admixed are diazines, benzothiadiazinones, 2,6-dinitroanilines, N-phenylcarbamates, biscarbamates, thiolcarbamates, halocarboxylic acids, triazines, amides, ureas, diphenyl ethers, triazinones, uracils, benzofuran derivatives, etc. Such combinations broaden the spectrum of action and sometimes synergistic effects are achieved. For instance, compositions may be prepared with the following compounds:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-,α,α,β,β-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate methyl-N-[3-(N'-3,4-difluorophenylcarbamoyloxy)-phenyl]-carbamate
methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicylco-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexhydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α,β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid,
sodium salt
2-[4-(3',5'-dichloropyridyl-2-oxy)-phenoxy]-propionic acid,
sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide 2-methyl-6-ethyl-N-(pyrazol-1-yl-methyl)-2-chloroacetanilide
2,6-dimethyl-N-(pyrazon-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2-(2-methyl-4-chlorophenoxy-N-methoxyacetamide
2-( -naphthoxy)-N,N-diethylpropionamide
2,2-diphenyl-N,N-dimethylacetamide-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
N-2,4-dimethyl-5-(trifluoromethyl)-sulfonylaminophenylacetamide
N-4-methyl-5-(trifluoromethyl)-sulfonylaminophenylacetamide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyldimethylaminosulfate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)

1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl-naphthoxyacetate
2-(2-methylphenoxy)-propionic acid (salts, esters, amides)
2-(4-chlorophenoxy)-propionic acid (salts, esters, amides)
2-(2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenocarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phosphorodithionate
2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide.

It may also be useful to apply the active ingredients, either alone or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies. Oils and oil concentrates, wetting agents, spreader-stickers and non-phytotoxic oils may be added to initiate the herbicidal action.

The influence of various representatives of the compounds according to the invention on the growth of unwanted and crop plants is demonstrated in the following greenhouse experiments.

The seeds of the test plants (cf. Table 1) were sown shallow, and separately, according to species. for the preemergence treatment, the active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated. No cover was placed on the vessels.

The pots were set up in the greenhouse—species from warmer areas at from 25° to 40° C., and species from moderate climates at 15° to 30° C. The experiments were run for 4 weeks. During this period, the plants were tended and their reactions to the various treatments assessed. The following tables contain the compounds investigated, the application rates in kg/ha of active ingredient, and the plants used for the tests. The scale used for assessment was 0 to 100, 0 denoting no damage or normal emergence, and 100 denoting nonemergence or complete destruction of at least the visible plant parts.

The following tables demonstrate the selective herbicidal action of the compounds according to the invention, which is directed mainly against unwanted grasses. The agents are excellently tolerated by some monocotyledonous and numerous dicotyledonous crops. The agents were applied both pre- and postemergence. A special application technique is to spray the active ingredients with the aid of spraying equipment in such a way that the leaves of sensitive crop plants are if possible not hit; the active ingredients reach the soil or unwanted plants growing below the crop plants (post-directed, lay-by treatment).

In view of the many application methods possible, the agents according to the invention, or mixtures containing them, may be used in addition to the crop plants listed in the tables in a large number of other crops for eliminating unwanted growth.

The following crop plants are given by way of example:

| Botanical name | Common name |
| --- | --- |
| *Allium cepa* | onions |

| Botanical name | Common name |
| --- | --- |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| Glycine max | soybeans |
| *Gossypium hirsutum* (*Gossypium arboreum* *Gossypium herbaceum* *Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| Malus spp. | apple trees |
| *Manihot esculenta* | cassava |
| *Medicago sativa* | alfalfa (lucerne) |
| *Mentha piperita* | peppermint |
| Musa spp. | banana plants |
| *Nicothiana tabacum* | tobacco |
| (*N. rustica*) | |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |
| Pinus spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | |
| *Ricinus communis* | |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | grain sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

| Botanical name | Abbreviation in tables | Common name |
| --- | --- | --- |
| *Allium cepa* | | onions |
| *Alopecurus myosuroides* | Alopec. mysor. | slender foxtail |
| *Amaranthus retroflexus* | | redroot pigweed |
| *Arachys hypogaea* | | peanuts (groundnuts) |
| *Beta vulgaris* | | sugarbeets |
| Brachiaria spp. | | signalgrass |
| *Brassica napus* | | turnips |
| *Bromus tectorum* | | downy brome |
| *Echinochloa crus galli* | Echninochl. c. g. | barnyardgrass |
| *Eleusine indica* | | goosegrass |
| *Euphorbia geniculata* | | South American member of the spurge family |
| Glycine max | | soybeans |
| *Gossypim hirsutum* | | cotton |
| Ipomoea spp. | | morningglory |
| *Lolium multiflorum* | | Italian ryegrass |
| *Lycopersicon esculentum* | Lycopersicon esculent. | tomatoes |
| *Pisum sativum* | | English peas |
| *Poa trivialis* | | bluegrass |
| *Sesbania exaltata* | | hemp sesbania |
| *Setaria faberia* | | giant foxtail |
| *Sinapis alba* | | white mustard |
| *Sorghum halepense* (aus Samen) | | Johnsongrass |
| *Triticum aestivum* | | wheat |

TABLE 2

Selective control of unwanted grasses; preemergence treatment in the greenhouse

Compound no. 56

| Test plants | % damage at approx. 1.0 kg/ha |
|---|---|
| *Allium cepa* | 3 |
| *Beta vulgaris* | 3 |
| *Brassica napus* | 0 |
| *Glycine max* | 0 |
| *Gossypium hirsutum* | 0 |
| *Pisum sativum* | 5 |
| Brachiaria spp. | 83 |
| *Echinochloa crus galli* | 87 |
| *Eleusine indica* | 100 |
| *Poa trivialis* | 90 |
| *Setaria faberi* | 84 |

0 = no damage
100 = plants destroyed

TABLE 3

Control of *Sorghum halepense* and other unwanted grasses in broadleaved crops; postemergence application in the greenhouse Compound no. 31

| Test plants | % damage at 1.0 kg/ha |
|---|---|
| *Arachys hypogaea* | 0 |
| *Brassica napus* | 10 |
| *Gossypium hirsutum* | 5 |
| *Lycopersicon esculent.* | 0 |
| *Alopec. myosur.* | 78 |
| *Bromus tectorum* | 90 |
| *Setaria faberi* | 80 |
| *Sorghum halepense* (from seed) | 87 |

0 = no damage
100 = plants destroyed

TABLE 4

Selective control of unwanted grass species in various crops; postemergence treatment in the greenhouse Compound no. 53

| Test plants | % damage at 1.0 kg/ha |
|---|---|
| *Arachys hypogae* | 0 |
| *Beta vulgaris* | 10 |
| *Brassica napus* | 0 |
| *Glycine max* | 10 |
| *Gossypium hirsutum* | 10 |
| *Lycopersicon esculent.* | 0 |
| *Triticum aestivum* | 0 |
| *Alopec. myosur.* | 80 |
| *Echinochloa crus galli* | 98 |

TABLE 4-continued

Selective control of unwanted grass species in various crops; postemergence treatment in the greenhouse Compound no. 53

| Test plants | % damage at 1.0 kg/ha |
|---|---|
| *Setaria faberi* | 98 |

0 = no damage
100 = plants destroyed

TABLE 5

Action of a prior art compound (disclosed in German Printed Application DE-AS 1,793,226) on postemergence treatment in the greenhouse

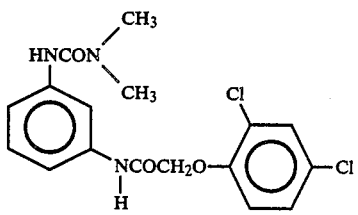

| Test plants | % damage at 1.0 kg/ha |
|---|---|
| *Arachys hypogaea* | 0 |
| *Beta vulgaris* | 5 |
| *Brassica napus* | 30 |
| *Glycine max* | 32.5 |
| *Gossypium hirsutum* | 34 |
| *Triticum aestivum* | 10 |
| *Alopec. myosur.* | 5 |
| Brachiaria spp. | 0 |
| *Echinochloa crus galli* | 0 |
| *Sorghum halepense* (from seed) | 0 |
| *Amaranthus retroflexus* | 10 |
| *Euphorbia geniculata* | 76 |
| *Ipomoea* spp. | 75 |
| *Sinapis alba* | 80 |
| *Sesbania exaltata* | 95 |

0 = no damage
100 = plants destroyed

This example shows how heavily the prior art compound damages the crop plants; its effectiveness is restricted to broadleaved plants

TABLE 6

Herbicidal action of further compounds on pre- and postemergence application in the greenhouse

| Compound no. | kg/ha | Preemergence | | Postemergence | |
|---|---|---|---|---|---|
| | | Lolium m. | Echinochl. c. g. | Lolium m. | Echinochl. c. g. |
| 3 | 3 | 100 | 100 | 100 | 90 |
| 6 | 3 | 90 | 90 | 80 | 90 |
| 9 | 3 | 90 | 100 | — | 90 |
| 42 | 3 | — | 100 | — | 90 |
| 43 | 3 | 90 | 100 | — | 90 |
| 60 | 3 | 90 | 100 | 100 | 100 |
| 61 | 3 | 90 | 100 | 100 | 90 |
| 63 | 3 | 90 | 100 | 100 | 100 |
| 64 | 3 | 80 | 100 | 100 | 90 |
| 77 | 3 | 100 | 90 | 90 | 100 |
| 32 | 3 | 100 | 90 | 90 | 100 |
| 66 | 3 | 100 | 100 | 90 | 100 |
| 78 | 3 | 100 | 100 | 90 | 95 |
| 79 | 3 | 100 | 80 | — | 100 |

EXAMPLE A 90 parts by weight of compound 1 is mixed with 10 parts by weight of N-methyl-α-pyrrolidone. A mixture is obtained which is suitable for application in the form of very fine drops.

EXAMPLE B 20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE C 20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE D 20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE E 20 parts by weight of compound 2 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE F 3 parts by weight of compound 3 is intimately mixed with 97 parts by weight of particulate kaolin. A dust is obtained containing 3% by weight of the active ingredient.

EXAMPLE G 30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE H 40 parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE I 20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. An m-anilido-urethane of the formula

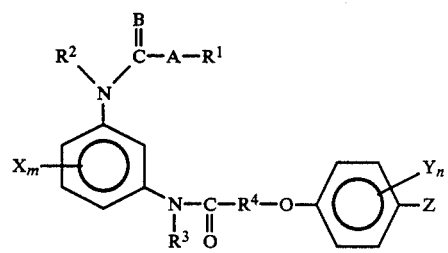

where
A and B independently of one another are oxygen or sulfur,
$R^1$ is alkyl of 1 to 5 carbon atoms, which is unsubstituted or substituted by chlorine, fluorine, methoxy or methoxycarbonyl, or is methylcyano or ethylcyano or is alkenyl of 2 to 4 carbon atoms which is unsubstituted or substituted by chlorine, or is alkynyl of 3 to 4 carbon atoms which is unsubstituted or substituted by chlorine or methoxy, or is cycloalkyl of 5 to 7 carbon atoms which is unsubstituted or substituted by alkyl of 1 to 4 carbon atoms, or is phenyl,
$R^2$ and $R^3$ are each independently of one another hydrogen, alkyl of 1 to 3 carbon atoms, and alkyl of 1 to 2 carbon atoms which is substituted by methoxy or halogen,
$R^4$ is alkylene of 1 to 6 carbon atoms which is unsubstituted or substituted by alkyl of 1 to 3 carbon atoms, methoxyalkyl or haloalkyl,
X is hydrogen, methyl, trifluoromethyl, methoxy, halogen, nitro or amino,
Y is hydrogen, alkyl of 1 to 3 carbon atoms, trifluoromethyl, haogen, methoxy, trifluoromethoxy, nitro, and Z is

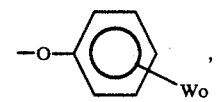

where W has, independently of Y, the meanings given for Y and
m, n and o are numbers from 1 to 4.

2. A process for combating the growth of unwanted plants, wherein the soil or the plants are treated with an m-anilido-urethane of the formula

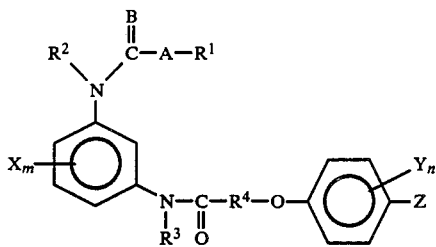

where
- A and B independently of one another are oxygen or sulfur,
- $R^1$ is alkyl of 1 to 5 carbon atoms, which is unsubstituted or substituted by chlorine, fluorine, methoxy or methoxycarbonyl or is methylcyano or ethylcyano or is alkenyl of 2 to 4 carbon atoms which is unsubstituted or substituted by chlorine, or is alkynyl of 3 to 4 carbon atoms which is unsubstituted or substituted by chlorine or methoxy, or is cycloalkyl of 5 to 7 carbon atoms which is unsubstituted or substituted by alkyl of 1 to 4 carbon atoms, or is phenyl,
- $R^2$ and $R^3$ are each independently of one another hydrogen, alkyl of 1 to 3 carbon atoms, and alkyl of 1 or 2 carbon atoms which is substituted by methoxy or halogen,
- $R^4$ is alkylene of 1 to 6 carbon atoms which is unsubstituted or substituted by alkyl of 1 to 3 carbon atoms, methoxyalkyl or haloalkyl,
- X is hydrogen, methyl, trifluoromethyl, methoxy, halogen, nitro or amino,
- Y is hydrogen, alkyl of 1 to 3 carbon atoms, trifluoromethyl, halogen, methoxy, trifluoromethoxy, nitro, and
- Z is

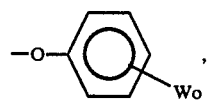

where W has, independently of Y, the meanings given for Y and m, n and o are numbers from 1 to 4.

3. An m-anilido-urethane selected from the group consisting of the compounds of the formulae

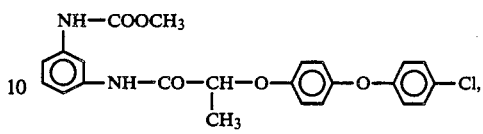

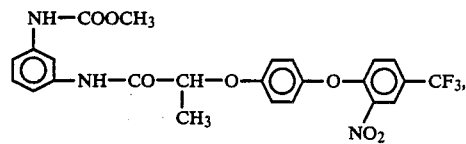

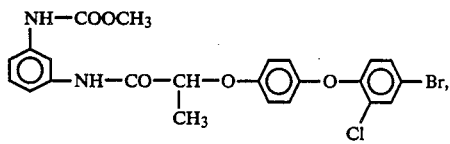

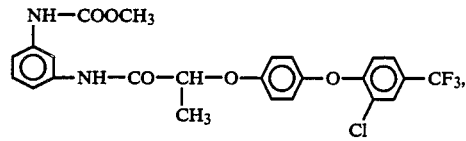

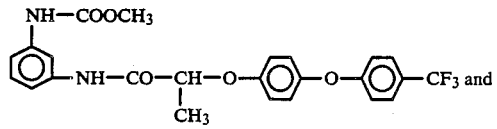

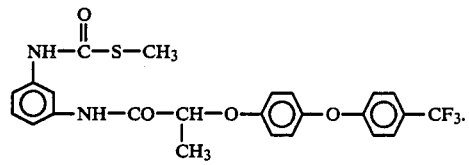

* * * * *